(12) United States Patent
Kang et al.

(10) Patent No.: US 8,906,074 B2
(45) Date of Patent: Dec. 9, 2014

(54) EXPANDABLE BONE FIXATION IMPLANT

(75) Inventors: Phillip Kang, Alameda, CA (US); Mark P. Grady, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 82 days.

(21) Appl. No.: 13/357,714

(22) Filed: Jan. 25, 2012

(65) Prior Publication Data

US 2012/0226320 A1    Sep. 6, 2012

Related U.S. Application Data

(60) Provisional application No. 61/436,028, filed on Jan. 25, 2011.

(51) Int. Cl.
*A61B 17/80* (2006.01)
*A61B 17/00* (2006.01)

(52) U.S. Cl.
CPC ... *A61B 17/8085* (2013.01); *A61B 2017/00867* (2013.01); *A61B 17/8076* (2013.01); *A61B 17/809* (2013.01)

USPC .............................. 606/283; 606/285; 606/76

(58) Field of Classification Search
USPC .................................................. 606/283–285
See application file for complete search history.

(56) References Cited

U.S. PATENT DOCUMENTS

| | | |
|---|---|---|
| 3,710,789 A | 1/1973 | Ersek |
| 5,250,048 A | 10/1993 | Gundolf |
| 2002/0032444 A1 | 3/2002 | Mische |
| 2002/0052568 A1 | 5/2002 | Houser |
| 2004/0087955 A1 | 5/2004 | Bordi |
| 2005/0171539 A1 | 8/2005 | Braun |
| 2009/0099409 A1 | 4/2009 | Luehrs |

FOREIGN PATENT DOCUMENTS

| | | |
|---|---|---|
| EP | 0475077 A2 | 3/1992 |
| FR | 2880794 A1 | 7/2006 |

*Primary Examiner* — Andrew Yang
(74) *Attorney, Agent, or Firm* — Baker & Hostetler LLP (57) ABSTRACT

Bone fixation devices, assemblies, and methods are provided. An expandable bone fixation implant can be implanted into a patient and attached to an underlying bone via a percutaneous or alternative fixation procedure in order to provide fixation and stabilization of the underlying bone.

21 Claims, 9 Drawing Sheets

EXPANDABLE BONE FIXATION IMPLANT

CROSS-REFERENCE TO RELATED APPLICATIONS

This claims the benefit of U.S. Patent Application Ser. No. 61/436,028 filed Jan. 25, 2011, the disclosure of which is hereby incorporated by reference as if set forth in its entirety herein.

BACKGROUND

Injuries to bones, such as fractures or breaks, are common in everyday life. For instance, in the case of fractured ribs, conventional surgical treatment includes the implantation of bone plates, bone wraps, and other methods of fixation and stabilization onto the fractured ribs. However, surgical procedures are typically open surgeries, which can be costly and time consuming, may involve the risk of surgical complications, and involve a prolonged recovery time. Furthermore, existing bone fixation devices, such as the above-mentioned bone plates and bone wraps, have been found to offer limited positional flexibility on the rib when implanted. As a result, surgical procedures are typically reserved for more severe trauma, such as those that involve fractures of multiple ribs. Other less severe rib fractures are typically treated conservatively, for example with pain medication and extended periods of rest, despite the reduced levels of functionality and long healing periods that commonly accompany such injuries.

SUMMARY

In accordance with one embodiment, an expandable bone fixation implant includes a implant body comprising a plurality of interconnected resilient links extending along a longitudinal axis between first and second ends and laterally between a bone-facing surface and an outer surface. The resilient links are configured such that the implant body is operable between a collapsed configuration configured to be implanted into a patient and an expanded configuration for engagement with an underlying bone.

BRIEF DESCRIPTION OF THE DRAWINGS

The foregoing summary, as well as the following detailed description, is better understood when read in conjunction with the appended drawings. For the purpose of illustrating the bone fixation implant and related method thereof, there is shown in the drawings exemplary embodiments; however, the bone fixation implant and related methods are not limited to the specific embodiments and methods disclosed. Like reference numerals refer to corresponding parts throughout the several embodiments of the drawings, in which:

FIG. 1A is attached to a fractured rib bone.

DETAILED DESCRIPTION

Certain terminology is used in the following description for convenience only and is not limiting. The words "right", "left", "top" and "bottom" designate directions in the drawings to which reference is made. The words "inward", "inwardly", "outward", "outwardly," "upward," "upwardly," "downward," and "downwardly" refer to directions toward or away from the geometric center of the device and/or designated parts thereof. The words, "anterior", "posterior", "superior", "inferior", "lateral", "medial", "sagittal", "axial", "coronal," "cranial," "caudal" and related words and/or phrases designate preferred positions and orientations in the human body to which reference is made and are not meant to be limiting. The terminology intended to be non-limiting includes the above-listed words, derivatives thereof and words of similar import.

Referring initially to FIGS. 1A-D, a bone fixation device in the form of an expandable bone fixation implant 100 is configured to provide fixation and stabilization of an underlying bone during healing after a fracture, break, or other injury to a bone 110, which can be a rib. For instance, the bone fixation implant 100 is configured to be attached to a bone 110 that has sustained one or more fractures, such as a fracture 112, that separates a first bone segment 110a from a second bone segment 110b. In particular, the fixation implant 100 is configured to be fixed to the bone 110 across the fracture 112 and to stabilize the fractured bone segments 110a-b by fixing the bone segments 110a-b with respect to each other. The fixation implant 100 is configured to be inserted minimally invasively into a body cavity of a patient that contains the bone 110 in an initial collapsed implantation configuration. Once the fixation implant 100 has been delivered to the implantation site, a percutaneous fixation procedure can be performed during which the fixation implant 100 can be expanded in the body cavity and positioned and fixed to the bone segments 110a-b on either side of the fracture 112, thereby stabilizing the injured bone 110.

The expandable bone fixation implant 100 includes an implant body 102 that extends along a longitudinal direction L, a lateral direction A that extends substantially perpendicular with respect to the longitudinal direction L, and a transverse direction T that extends substantially perpendicular to both the longitudinal direction L and the lateral direction A. The implant body 102 is elongate in the longitudinal direction L along a central longitudinal axis LL, defines a width in the lateral direction A, and defines a height in the transverse direction T. It should be appreciated that the longitudinal and lateral directions L and A, respectively, extend horizontally and the transverse direction T extends vertically in the orientation illustrated in FIG. 1A. Accordingly, while certain directional terms are used herein to describe the expandable bone fixation implant 100 as illustrated for the purposes of clarity and convenience, it should appreciated that these orientations of the expandable bone fixation implant 100 may change during use. It should be further appreciated that the implant body 102 extends radially outward along a radial direction R from the central longitudinal axis LL along a direction that can include both lateral and transverse directional components.

Figure 1A:
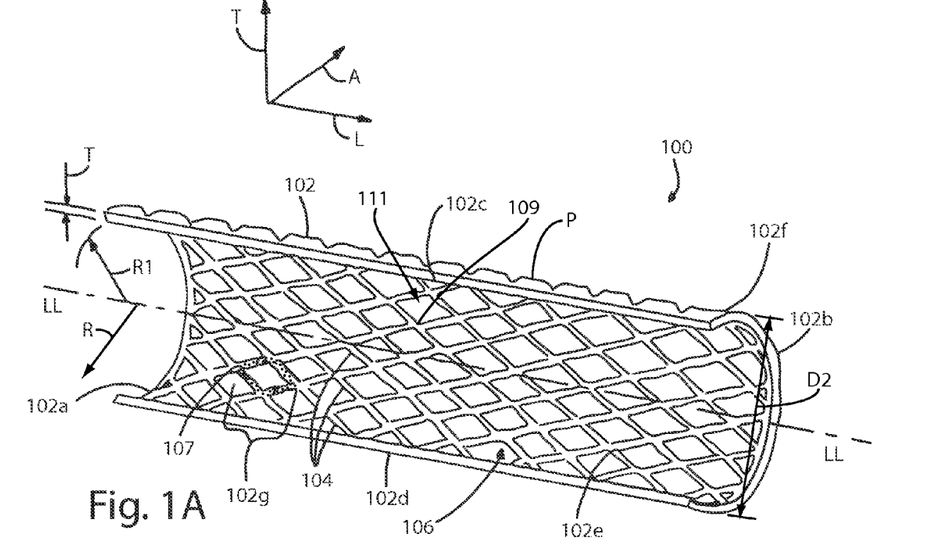
FIG. 1A is a perspective view of an expandable bone fixation implant configured in accordance with one embodiment.

With continuing reference to FIG. 1A, the implant body 102 is resilient and expandable from a first collapsed configuration having a first outer cross-sectional dimension D1 (see FIGS. 2A-B) to a second expanded configuration having a second outer cross-sectional dimension D2 that is greater than the first outer cross-sectional dimension D1. The first and second outer cross-sectional dimensions can be radial dimensions, for instance at least one or both of a height or a width. The first and second outer cross-sectional dimensions can be defined by a straight line that is substantially perpendicular to the longitudinal direction L, and can pass through the central longitudinal axis LL or be offset from the central longitudinal axis LL. The implant body 102 can also be collapsible from the second expanded configuration to the first collapsed configuration. In accordance with one embodiment, the implant body 102 can be constructed of a resilient material having shape memory characteristics, such as nitinol or the like, but can also be constructed of any other biocompatible and/or bioresorbable material as desired, such as low grade titanium, commercially pure titanium, plastic, polyether ether ketone (PEEK), polyetherketoneketone (PEKK), polyglycolic acid (PGA), polylactic acid (PLA), polydioxanone (PDS), and the like.

Figure 1B:
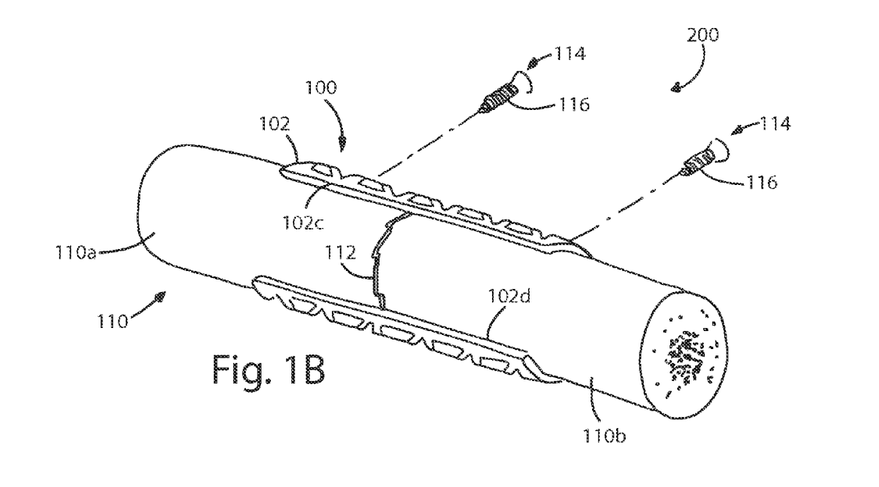
FIG. 1B is a perspective view of the expandable bone fixation implant illustrated in FIG. 1A shown attached to an underlying bone.
Figure 1C:
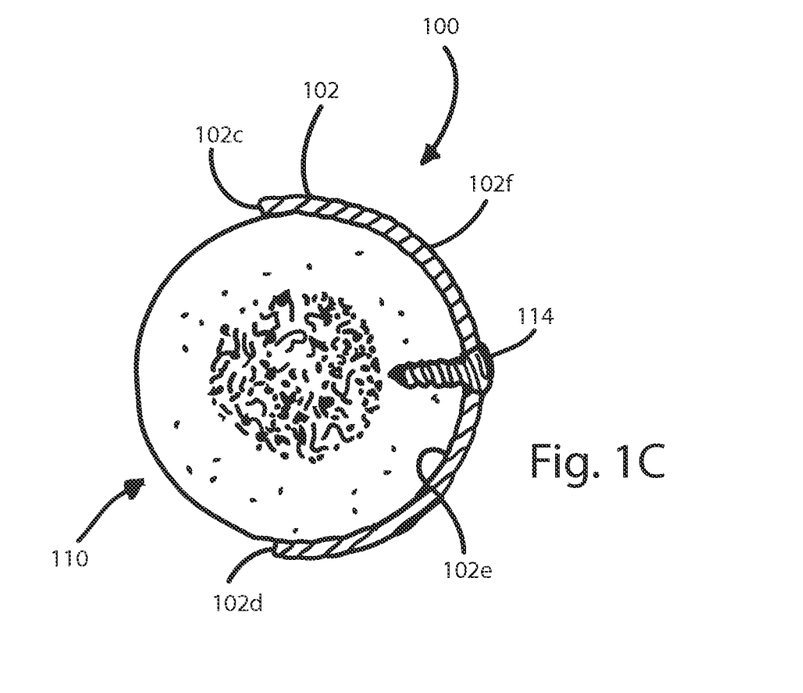
FIG. 1C is a sectional end elevation view of the expandable bone fixation implant illustrated in FIG. 1A, attached to an underlying bone.

Referring also to FIG. 1B, the implant body 102 is illustrated as defining a first outer end 102a and a second outer end 102b opposite the first outer end 102a and spaced from the first outer end 102a along the longitudinal direction L. The implant body 102 can be substantially C-shaped when in the second expanded configuration, so as to define a first or upper transverse edge 102c and a second or lower transverse edge 102d that is spaced from the first or upper transverse edge 102c along the transverse direction T (or the lateral direction A or combination of the lateral direction A and transverse direction T depending on the gap between the edges 102c-d and the orientation of the implant body 102). Thus, the upper and lower transverse edges 102c and 102d can be referred to as first and second circumferential outer edges, respectively. The implant body 102 further defines a first or inner radial surface 102e and a second or outer radial surface 102f that is opposite the inner radial surface 102e and outwardly spaced from the inner radial surface 102f along the radial direction R. The inner, or bone-facing, surface 102e faces inwardly toward the underlying bone 110 to which the implant body 102 is attached, and the outer surface 102f faces outwardly away from the inner surface 102e. The inner surface 102e of the implant body 102 can be coated with bone morphogenic protein (BMP) or any other bone growth enhancing material, so as to enhance bone regrowth in the underlying bone. The implant body 102 can define the first and second outer dimensions as measured from radially opposed locations on the outer surfaces 102f along a straight line that can pass through the central longitudinal axis LL, or can alternatively be offset from the central longitudinal axis LL.

The implant body 102 defines a radial thickness T that extends between the inner and outer surfaces 102e-f, respectively, along the radial direction R. The implant body 102 can be constructed having a substantially uniform thickness T throughout, for instance between the first and second ends 102a-b, and between the upper and lower transverse edges 102c-d, respectively, as illustrated. Alternatively, the implant body 102 can be constructed with one or more sections of varying thickness T, for example to induce desired deformation characteristics, strength, or the like into the implant body 102. In a preferred embodiment, the thickness T of the implant body 102 ranges from about 1 mm to 3 mm, and is preferably about 1.5 mm.

With continuing reference to FIGS. 1A-D, the expandable bone implant body 102 can be curved between the upper and lower transverse edges 102c-d, so as to define a substantial C-shape that allows the inner surface 102e of the implant body 102 to generally conform to the external surface of an underlying bone 110. The implant body 102 can thus be curved about the longitudinal axis LL. In the illustrated embodiment, the implant body 102 is substantially arc-shaped about the longitudinal axis LL between the upper and lower transverse edges 102c-d, thus defining a generally "C-shaped," semi-tubular shape that is open between the upper and lower transverse edges 102c-d. Otherwise stated, the implant body 102 can be circumferentially discontinuous about the central longitudinal axis LL, so as to define a discontinuous outer perimeter P, when the implant body 102 is in the expanded configuration. The arc-shaped curvature of the implant body 102 can be defined by a radius R1 that extends along the radial direction R from the longitudinal axis LL to the inner surface 102e. In the illustrated embodiment, the length of the radius R1 can remain constant both with respect to the lateral direction around the longitudinal axis LL between the upper and lower transverse edges 102c-d of the implant body 102, and with respect to the length of the implant body 102 as defined between the first and second outer ends 102a-b, such that the cross-sectional curvature of the implant body 102 is uniform throughout the implant body 102. It should be appreciated that the length of the radius R1 and/or the length of the implant body 102 can be defined based on the anatomy of the intended underlying bone 110 to which the implant will be attached, the amount of surface area on the underlying bone 110 to be fixedly enwrapped by the inner surface 102e of the implant 100, and the like.

It should be appreciated that the implant body 102 can also be configured such that the length of the radius R1 varies along one or more sections of the implant body 102 with respect to the lateral direction around the longitudinal axis LL between the upper and lower transverse edges 102c-d of the implant body 102, and/or varies along one or more sections of the length of the implant body 102, thereby defining an implant body 102 with non-uniform cross-sectional curvature. It should further be appreciated that although the illustrated embodiment of the implant body 102 extends in a straight longitudinal direction between the first and second outer ends 102a-b, that the implant body 102 can also be laterally curved between the first and second outer ends 102a-b, for instance with respect to one or more transverse axes, and/or can be transversely curved between the first and second outer ends 102a-b, for instance with respect to one or more lateral axes. Accordingly, it should be appreciated that the implant body 102 can be configured using any combination of longitudinal, lateral, and/or transverse curvature, for example to ensure that contact between the inner surface 102e of the implant body 102 and the outer surface of the underlying bone is optimized, thereby optimizing the stabilization and fixation provided by the expandable bone fixation implant 100 to the underlying bone.

The opening between the upper and lower edges 102c-d can be spaced apart through a uniform or varying distance along the length of the implant body 102, and the upper and lower edges 102c-d can be configured with any edge geometry as desired. For instance, the distance between the upper and lower edges 102c-d and the geometry of the edges can be configured based upon the amount of the outer surface of the underlying bone 110 that should be encompassed within the implant body 102, the presence of ligaments, muscles, and/or other bodily tissues that might obstruct contact between the implant body 102 and the underlying bone, and other such considerations. It should therefore be appreciated that while the upper and lower edges 102c-d of the illustrated embodiment are substantially straight between the first and second ends 102a-b, respectively, that the upper and lower edges 102c-d can be configured with any alternate geometry as desired. It should further be appreciated that the implant body 102 can be configured such that one or more sections, up to the entirety, of the length of the upper and lower edges 102c-d engage with each other when the implant body 102 is attached to an underlying bone, and thus that one or more distinct openings between the upper and lower edges 102c-d, or no opening at all, can be defined. Moreover, it should be appreciated that one or more sections, up to the entirety, of the length of the upper and lower edges 102c-d, can be configured to overlap each other when the implant body 102 is attached to an underlying bone, and further that one or more of the overlapping sections of the upper and lower edges 102c-d can be configured to complimentarily engage with each other.

The implant body 102 includes a plurality of interconnected resilient flexible links 104 that can be integral and monolithic with each other as illustrated, or can alternatively be discreetly attached to each other. The links 104 can be interconnected at intersections 109 in a repeating pattern to define a resilient, expandable and collapsible lattice or mesh 106 that define openings 111 in the implant body 102. The mesh 106 can be defined throughout a substantial entirety of the implant body 102 as illustrated, or alternatively can be defined in one or more distinct portions of the implant body 102. In addition to allowing the implant body 102 to be collapsed for implantation into a patient and subsequently expanded so as to conform to the outer surface of the bone 110 as described in more detail below, once the implant body 102 has been attached the bone 110, the mesh 106 allows for bony in-growth during the healing process of the bone 110. It should be appreciated that while the links 104 are diamond shaped in accordance with the illustrated embodiment, the links 104 can define any suitable alternative geometry as desired. It should be further appreciated that the links 104 can be symmetrical or asymmetrical with respect to each other and can be arranged in a repeating or variable pattern, as illustrated, and that the implant body 102 can be constructed with any combination of differing link geometries and/or interconnection patterns as desired.

Figures 2A, 2B:
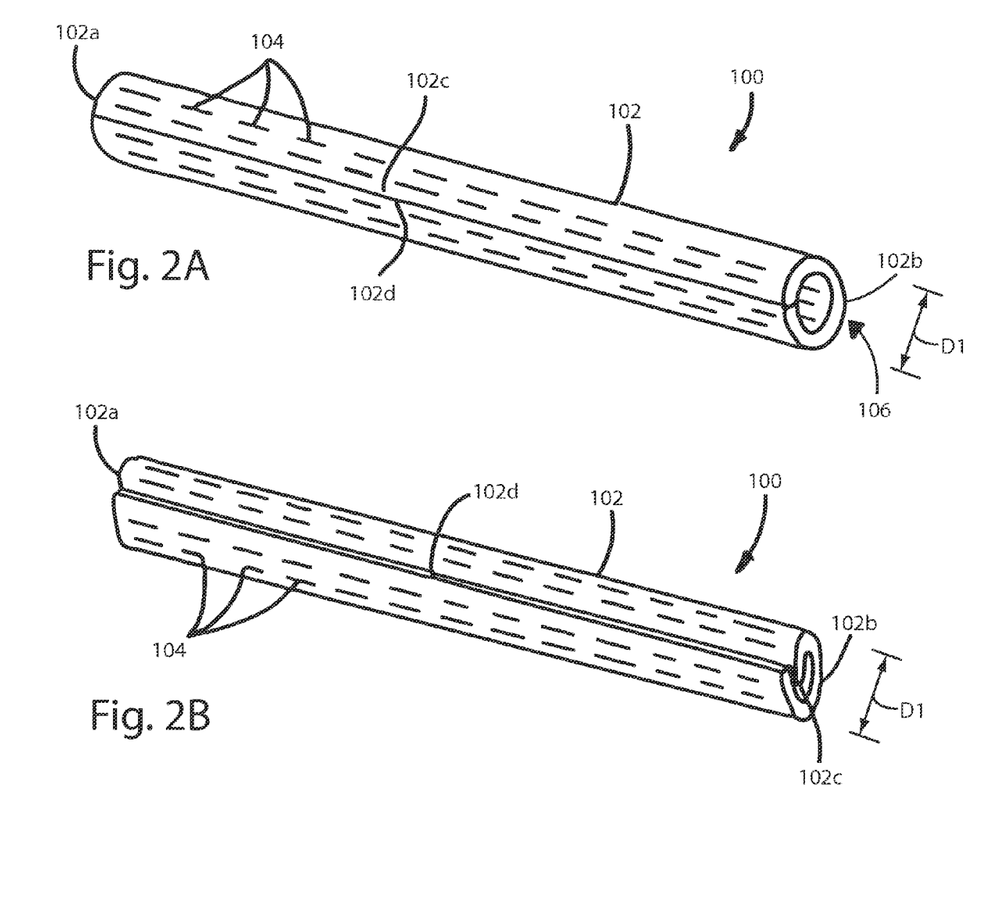
FIG. 2A is a perspective view of the expandable bone fixation implant illustrated in FIG. 1A shown in a first collapsed configuration.
FIG. 2B is a perspective view of the expandable bone fixation implant illustrated in FIG. 1A shown in a second collapsed configuration.

Referring now to FIGS. 1A and 2A-B, the links 104 can be configured as resilient links 104 such that the links 104 can be at least partially collapsed upon themselves, thereby allowing the implant body 102 to be operatively expanded and contracted between an expanded, or neutral, configuration as illustrated in FIG. 1A, and a contracted, or collapsed, configuration as illustrated in FIGS. 2A-B. The collapsed configuration displaces a smaller volume than the expanded configuration, such that the implant body 102 can be implanted into a patient when in the collapsed configuration, for example via a catheter, as described in more detail below. Otherwise stated, the implant body 102 defines a larger cross section in the expanded configuration than in the collapsed configuration. For instance, when the implant body is in the expanded configuration, the openings 111 define a first circumferential or tangential dimension, and when the implant body is in the collapsed configuration, the openings 111 define a second circumferential or tangential dimension that is less than the first circumferential or tangential dimension.

Referring to FIG. 2A, the implant body 102 is radially collapsible from an expanded configuration to a collapsed configuration, such that the upper and lower transverse edges 102c-d abut each other and a hollow channel 108 extends through the implant body 102 from the first through the second ends 102a-b, respectively, along the longitudinal direction. The hollow channel 108 can be encircled by the implant body 102. Alternatively, the upper and lower transverse edges 102c-d can be spaced apart so as to define a circumferential or tangential opening therebtween when the implant body 102 is in the collapsed configuration (see FIG. 3A). The implant body 102 can then be iterated from the collapsed configuration illustrated in FIG. 2A to an expanded configuration by expanding an expandable bladder 126, such as a bladder that is disposed in the channel 108 as described in more detail below (see FIG. 3B). Alternatively still, referring to FIG. 2B, the transverse edges 102c-d can be disposed past each other so as to define a smaller encircled channel 108 than when the transverse edges 102c-d abut each other. For instance, the implant body 102 can be radially collapsed and rolled upon itself into the collapsed configuration. The implant body 102 can define an initial collapsed configuration prior to implantation, or can define an initial expanded configuration that can be collapsed prior to implantation. Thus, the implant body 102 can be relaxed in the expanded configuration. The implant body 102 can be iterated from the collapsed configuration illustrated in FIG. 2B to the expanded configuration with the use of one or more percutaneously inserted tools or instruments, such as a grasper tool or a mandrel, as described in more detail below.

It should be appreciated that depending upon what material is used to construct the implant body 102, that the implant body 102 may have shape memory characteristics such that the implant body 102 can expand at least partially, or completely unassisted, from the collapsed configuration to the expanded configuration, for instance when the implant body 102 is removed from a delivery sheath after being inserted into a patient. It should further be appreciated that the collapsed configurations of the implant body 102 are not meant to be limited to the example collapsed configurations depicted in FIGS. 2A-B, and that the implant body 102 can be configured with any alternative collapsed configuration as desired.

Referring to FIGS. 1A-D and FIG. 7 generally, an implant assembly 200 can include the implant body 102, an implantation assembly including an insertion instrument 400, a second instrument 500 that is can be configured as a bone screw dispensing and/or bone screw driving tool or a second grasper tool, a catheter 300, and a plurality of fasteners, including one or more bone anchors 114 illustrated as bone screws 116 that are configured to fix the implant body 102 to an underlying structure, such as the bone 110. Of course the bone anchors 114 can be provided as any other type of fastener as desired. The bone anchors 114 can be percutaneously or otherwise be delivered to the location where the implant body 102 will be attached to the underlying bone 110 and driven into place via a bone screw dispensing and/or driving tool (not shown).

Referring to FIGS. 1A-D and 3A-B, according to one embodiment, the bone anchors 114 can be bone screws that are tethered to the implant body 102, and thus designed to be permanently attached to the implant body 102. Accordingly, the implant body is attached to the bone 110 when the bone anchors 114 are affixed to the bone 110, as described in more detail below. Alternatively, the implant body 102 and/or the bone anchors 114 can be configured such that the bone anchors 114 can be removably coupled to the implant body 102 during implantation of the implant body 102 onto the bone 110. For example, the heads of the bone anchors 114 can be configured to be press fit to the ends of the implant body 102, or the bone anchors 114 can be configured to be received in complimentary retaining structures defined on the implant body 102, such as complimentary slots or grooves.

Figure 1D:
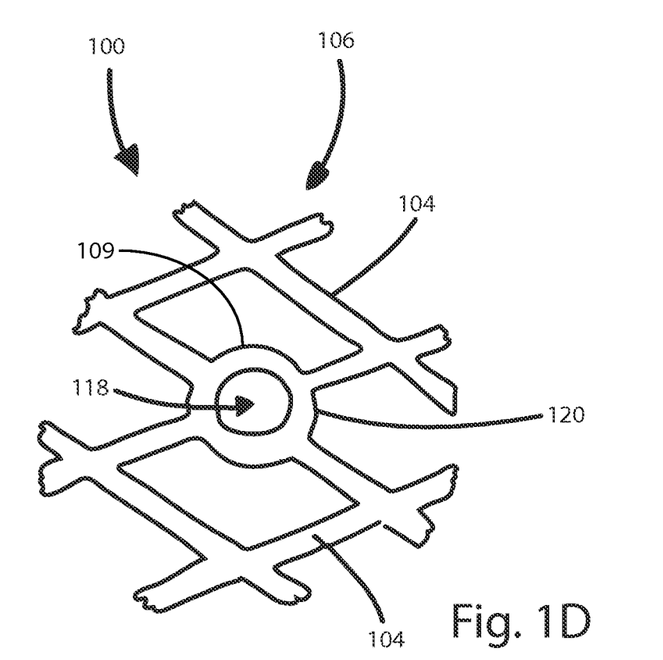
FIG. 1D is a side elevation view of a portion of the implant body of the expandable bone fixation implant illustrated in FIG. 1A, configured in accordance with an alternative embodiment.

In accordance with the illustrated embodiment, the bone screws 116 can be at least partially disposed in the openings provided by the links 104 at any location on the implant body 102 and driven into place within the underlying bone 110. Alternatively, the implant body 102 can be configured with a plurality of bone attachment locations 120. As depicted in FIG. 1D, the bone attachment locations 120 are provided as screw holes 118 extending laterally through the implant body 102, for instance at one or more of the intersections 109. It should be appreciated that while the bone attachment locations 120 are depicted as being located at the intersections 109 of adjacent interconnected links 104, that the bone attachment locations 120 can be located anywhere on the implant body 102 as desired.

Figure 4:
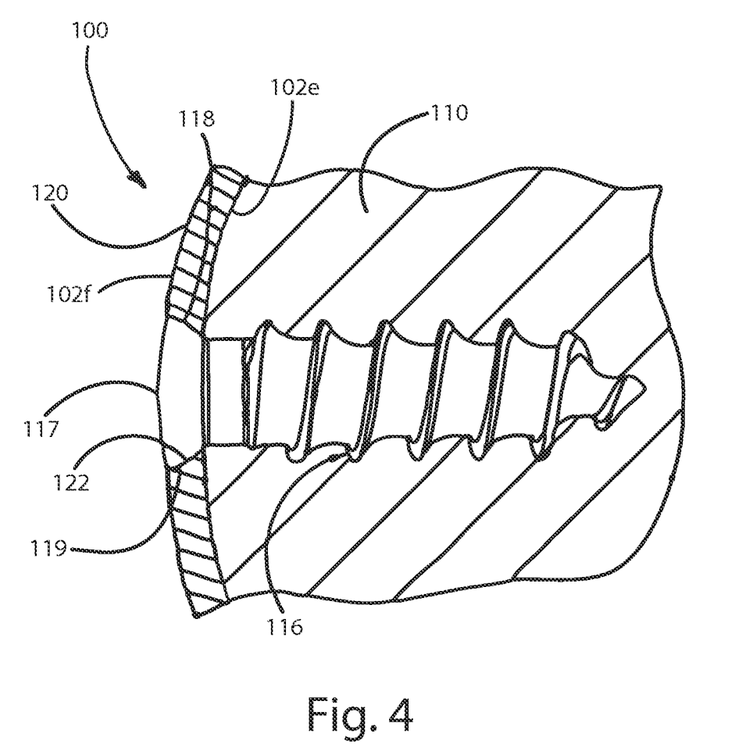
FIG. 4 is an enlarged sectional end elevation view of the expandable bone fixation implant as illustrated in FIG. 1C, shown attached to an underlying bone.

The screw holes 118 can be sized to threadedly or non-threadedly receive corresponding fasteners or bone anchors 114, such as the bone screws 116. Specifically, referring to FIG. 4, each bone attachment location 120 on the implant body 102 can include a beveled inner surface 122 that defines the screw hole 118, and is sized and shaped to receive a correspondingly beveled inwardly facing surface 119 of the screw head 117 of a bone screw 116. The beveled surface 122 is positioned such that the outwardly facing surface of the screw head 117 aligns with the outer surface 102f of the implant body 102 when the screw head 117 is fully seated in the screw hole 118. As illustrated, the screw head 117 is flush with the outer surface 102f of the implant body 102, though the screw head 117 could alternatively be inwardly recessed or slightly outwardly protruding with respect to the outer surface 102f of the implant body 102. Accordingly, the screw head 117 can compress the implant body 102 against the underlying bone 110. It should be appreciated that the screw hole 118 can assume any one of numerous configurations. For example the inner surface 122 can be beveled, straight, or can be rounded at any desired radius. In another example configuration, the inner surface 122 can be threaded, the threads configured to engage complimentary threads formed on the inwardly facing surface 119 of the screw head 117, such that the bone screw 116 is self-locking within the screw hole 118. It should also be appreciated that the bone screws 116 can be self-drilling, or can alternatively be insertable into pre-drilled holes.

Figure 3A:
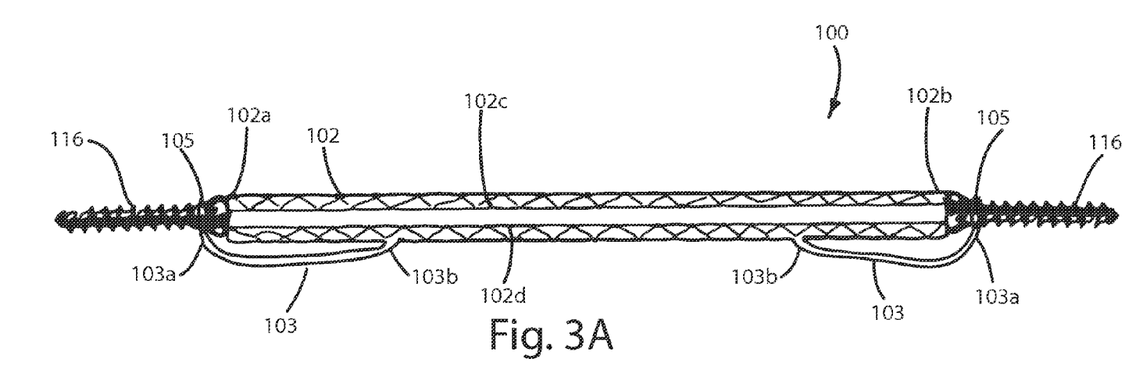
FIG. 3A is a sectional side elevation view of the expandable bone fixation implant illustrated in FIG. 2A, including a pair of tethered bone screws.
Figure 3B:
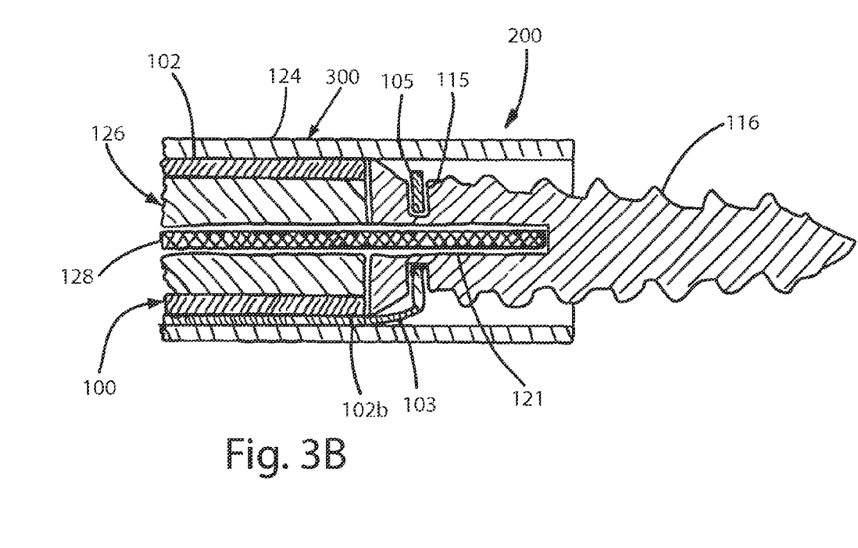
FIG. 3B is a sectional elevation view of a portion of an implant assembly including a portion of the expandable bone fixation implant, and other components.

Referring now to FIGS. 3A-B, the implant 100 can include the bone screws 116 tethered to the implant body 102 such that the bone screws 116 are implanted along with the implant body 102. Tethering the bone screws 116 to the implant body 102 can prevent perioperative or subsequent loss of the bone screws 116 in the patient's body. In the illustrated embodiment, the bone screws 116 are tethered to the implant body 102 via tethers 103. The tethers 103 can be constructed with any desired structure, such as a solid wire, flexible rod, a plurality of linked segments, and the like, and can be constructed of any appropriate biocompatible material, including non-bioresorbable materials such as nitinol, nylon, polypropylene, and the like, or bioresorbable materials such as polyglycolic acid (PGA), polylactic acid (PLA), polydioxanone (PDS), and the like.

The illustrated tethers 103 define proximal ends 103a that are connected to the bone screws 116 and distal ends 103b that are opposite the proximal ends 103a and connected to the implant body 102. The implant body 102 can be constructed such that the distal ends 103b of the tethers 103 are integral and monolithic with the implant body 102 at desired locations along its length, such that the tethers 103 and/or respective bone screws 116 are components of the expandable bone fixation implant 100. Alternatively, the tethers 103 can be attached to the bone screws 116 and to desired locations on the implant body 102 when the implant 100 is implanted. Alternatively still, the bone screws 116 can be provided with the tethers 103 pre-attached to the bone screws 116, and the distal ends 103b of the tethers 103 can be attached to desired locations on the implant body 102 at the time of implantation. It should be appreciated that the tethers 103 can be attached to the implant body 102 when the implant body 102 is in either the collapsed configuration or the expanded configuration. The tethers 103 can be of any length sufficient to allow insertion of a bone screw 116 through a respective desired location on the implant body 102 and into the underlying bone.

In the illustrated embodiment, the tethers 103 have attachment rings 105 coupled to their proximal ends 103a. The attachments rings 105 are configured to be disposed in complimentary grooves 115 defined in the bone screws 116. The attachment rings 105 and the grooves 115 are complimentarily sized such that the bone screws 116 are free to rotate with respect to the tethers 103 when the attachment rings 105 are disposed in the grooves 115.

Referring now to FIG. 3B, the expandable bone fixation implant 100, tethers 103 and/or respective bone screws 116 can be combined with various other components of the implant assembly 200. For example, the implant body 102 can be iterated to the collapsed configuration as depicted, and inserted, along with a pair of tethered bone screws 116, into a flexible sheath 124, such as that of a catheter 300. The implant assembly 200 can include an expansion device, such as expandable inflatable bladder 126 illustrated as an inflatable balloon, disposed within the implant body 102, for instance in the channel 108, and configured to iterate the implant body 102 from the collapsed configuration to the expanded configuration after the implant body 102 has been implanted. The expansion device can also be provided as a mandrel (not shown) disposed within the collapsed implant body 102. After the plated body 102 has been implanted, the mandrel can be pulled trough the implant body 102, for instance from the second end 102b to the first end 102a, thereby iterating the implant body 102 from the collapsed configuration to the expanded configuration. The implant assembly 200 can further include a guide wire 128 disposed within the bladder 126, and thus the implant body 102 and the sheath 124, as illustrated. The guide wire 128 can lend rigidity to the implant assembly 200 and assist a surgeon in guiding the implant assembly 200 into a target location in a patient's body.

The bone screws 116 may be specifically configured for use with the implant body 102. For instance, as illustrated, respective first and second bone screws 116 are tethered to the implant body 102 and disposed at the first and second ends 102a-b of the implant body 102, respectively. The second bone screw 116, disposed at the second end 102b of the implant body 102, includes a longitudinal bore 121, the bore 121 configured to receive the guide wire 128 therein. In the first bone screw 116, disposed at the first end of the implant body 102, the bore 121 can be extended throughout the entire longitudinal length of the bone screw 116, such that the guide wire 128 can be inserted through the first bone screw 116, through the bladder 126, and into the bore 121 of the second bone screw 116.

Referring again to FIG. 1A, the implant body 102 can include additional securement structures to enhance engagement between the inner surface 102e of the implant body 102 and the outer surface of the underlying bone to which the implant body 102 is attached. For example, the implant body 102 can include at least one grip member 102g, such as spikes 107, that extend radially inward from the inner surface 102e toward the central longitudinal axis LL. It should be appreciated that the grip members 102g can be provided on one or more sections, up to the entirety, of the inner surface 102e of the implant body 102, as desired. The grip members 102g, and in particular the spikes 107 of the illustrated embodiment, can be configured to engage or bite into underlying structure, such as the outer surface of the underlying bone 110. The grip members 102g can increase the surface area of the inner surface 102e which can be coated with bone growth enhancing materials such as BMP. Of course, the implant 100 can include any bone growth enhancing coating applied to a portion of the inner surface 102e, for instance at distinct areas of the inner surface 102e, up to the entirety of the inner surface 102e, as desired.

The implant body 102 can include additional or alternative securement structures along the upper and lower transverse edges 102c-d. For example, one or more grip members, such as teeth, can extend inwardly from the upper and/or lower transverse edges 102c-d in a direction towards the underlying bone, the teeth configured to engage the outer surface of the underlying bone. The teeth can be constructed so as to remain in a fixed position with respect to the implant body 102, or alternatively can be constructed so as to fold out, or otherwise be iterated to a deployed configuration, after implantation of the implant body 102.

Referring now to FIGS. 5A-F, the expandable bone fixation implant 100 can include an implant body 202 constructed in accordance with an alternative embodiment. The implant body 202 is illustrated as defining opposed first and second longitudinally outer ends 202a and 202b, opposed upper and lower longitudinal edges 202c and 202d, and opposed inner and outer lateral surfaces 202e and 202f. The inner, or bone-facing, surface 202e faces inwardly toward an underlying bone to which the implant body 202 is attached, and the outer surface 202f faces outwardly away from the inner surface 202e. The bone-facing surface 202e of the implant body 202 can be coated with BMP or other bone growth enhancers as desired. The implant body 202 defines a lateral thickness T between the inner and outer surfaces 202e-f, respectively. The implant body 202 can be constructed having uniform thickness T throughout, for instance between the first and second ends 202a-b, respectively and between the upper and lower edges 202c-d, respectively, as illustrated. Alternatively, the implant body 202 can be constructed with one or more sections of varying thickness T, for example to induce desired deformation characteristics, strength, or the like into the implant body 202. In a preferred embodiment, the thickness T of the implant body 202 ranges from about 1 mm to 3 mm, and is preferably about 1.5 mm.

Figures 5A, 5B:
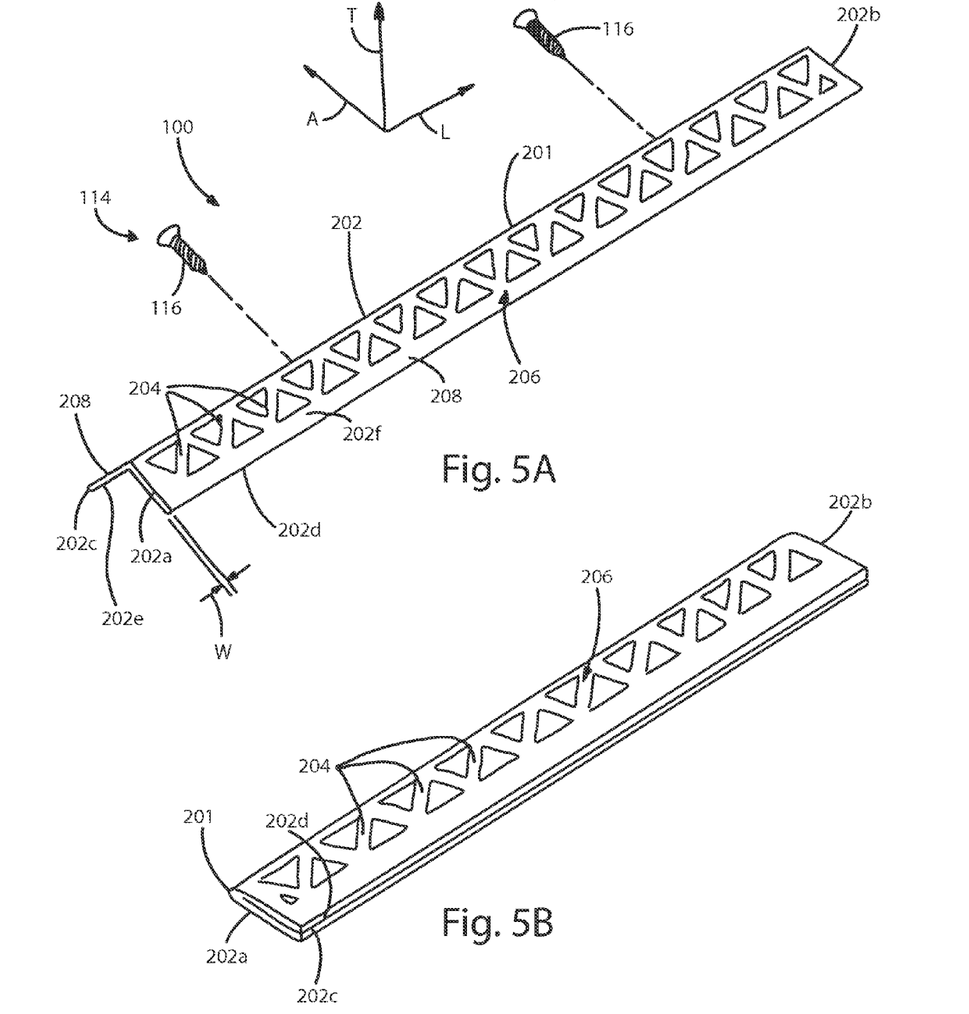
FIG. 5A is a perspective view of an expandable bone fixation implant constructed in accordance with an alternative embodiment.
FIG. 5B is a perspective view of the expandable bone fixation implant illustrated in FIG. 5A shown in a collapsed configuration.
Figure 5C:
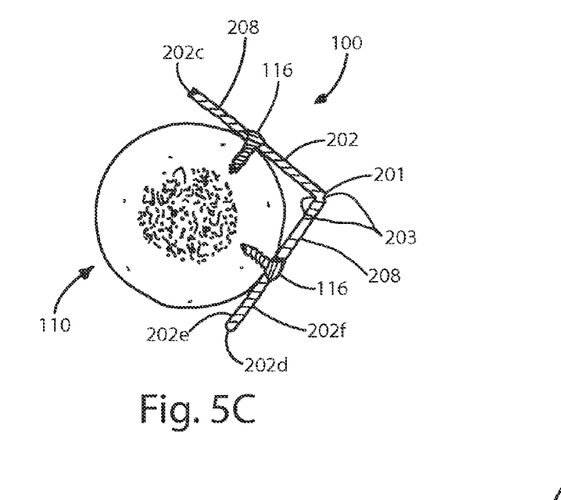
FIG. 5C is a sectional end elevation view of the expandable bone fixation implant illustrated in FIG. 5A, attached to an underlying bone.
Figure 5D:
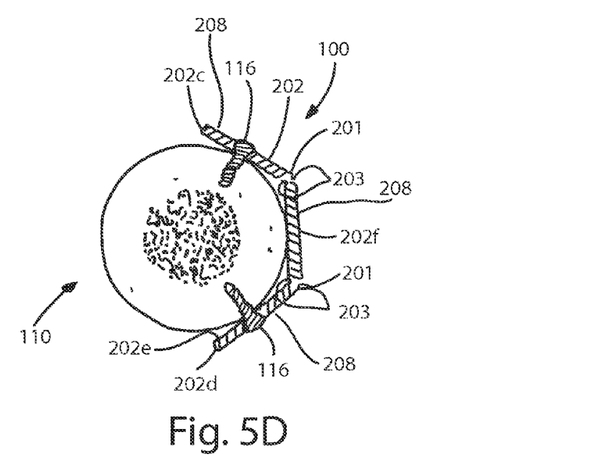
FIG. 5D is a sectional elevation view of the expandable bone fixation implant illustrated in FIG. 5C, constructed in accordance with an alternative embodiment and attached to an underlying bone.
Figure 5E:
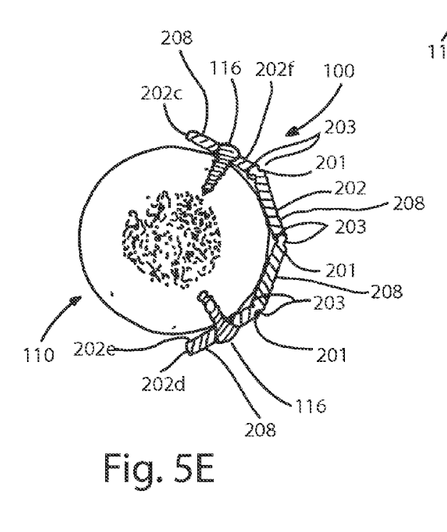
FIG. 5E is a sectional elevation view of the expandable bone fixation implant illustrated in FIG. 5D, constructed in accordance with another alternative embodiment and attached to an underlying bone.
Figure 5F:
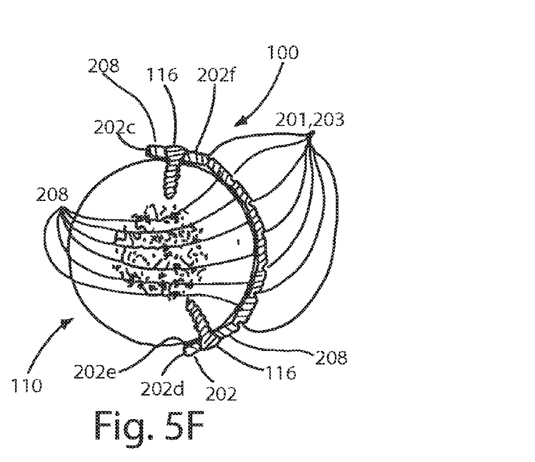
FIG. 5F is a sectional elevation view of the expandable bone fixation implant illustrated in FIG. 5E, configured in accordance with still another alternative embodiment and attached to an underlying bone.

The implant body 202 includes a plurality of interconnected resilient links 204 that can be integrally connected as illustrated, or can alternatively be discreetly attached to each other. The links 204 can be interconnected in a repeating pattern to define a resilient lattice, or mesh 206, in the implant body 202. The mesh 206 can be defined throughout substantially the entirety of the implant body 202 as illustrated, or alternatively can be defined in one or more distinct portions of the implant body 202. The mesh 206 can be configured to influence the flexibility of the implant body 202 and thus the ability of the inner surface 202e of the implant body 202 to conform to the outer surface of an underlying bone. It should be appreciated that while the links 204 in the illustrated embodiment are triangle shaped, that any other geometry can be used for the links 204 as desired. It should be further appreciated that the links 204 need not be symmetrical with respect to each other as illustrated, or be arranged in a repeating pattern, and that the implant body 202 can be constructed with any combination of differing link geometries and/or interconnection patterns as desired.

The implant body 202 can be attached, or secured, to an underlying structure, such as an underlying bone 110, with one or more fasteners or bone anchors 114, such as the bone screws 116 illustrated in FIGS. 1A-D and FIG. 4. Of course any other type of fastener or bone anchor 114 can be used as desired. The bone screws 116 can be implanted and driven into the underlying bone 110 via any suitable bone screw dispensing and/or driving tool. Alternatively, the bone screws 116 can be tethered bone screws that are integrally connected or otherwise coupled to the implant body 202, as described above with reference to FIGS. 3A-B. In accordance with the illustrated embodiment, the bone screws 116 can be at least partially disposed in openings in the mesh 206 at any location on the implant body 202 and driven into place the underlying bone 110. Alternatively, the implant body 202 can include a plurality of bone attachment locations, as described above with reference to FIG. 1D. Similarly the bone attachment locations can be provided as screw holes extending laterally through the implant body 202, as described above with reference to FIG. 4, and can be located anywhere on the implant body 202 as desired. It should be appreciated that when the implant body 202 is attached to an underlying bone, that the mesh 206 can allow for bony in-growth during the healing process of the bone.

The implant body 202 further includes a longitudinal folding edge 201 defined along the longitudinal direction L between the first and second ends 202a-b, respectively. The folding edge 201 longitudinally divides the implant body 202 into first and second plate segments 208 that can be equally dimensioned as illustrated. The folding edge 201 allows the implant body 202 to be iterated between the expanded configuration illustrated in FIG. 5A and the collapsed configuration illustrated in FIG. 5B for implantation into a patient. In the illustrated embodiment, the folding edge 201 is defined between the first and second ends 202a-b, respectively, substantially along the midline of the implant body 202 as defined between the upper and lower edges 202c-d. It should be appreciated that the folding edge 201 can be alternatively be defined at any desired location between the upper and lower edges 202c-d as desired.

When the implant body 202 of the illustrated embodiment is in the collapsed configuration, the implant body 202 is folded substantially in half around the folding edge 201 such the first and second plate segments 208 abut each other, thus aligning the upper and lower edges 202c-d. It should be appreciated that the folding edge can be located anywhere along the implant body as desired. The collapsed configuration displaces a smaller volume than the expanded configuration, such that the implant body 202 can be implanted into a patient when in the collapsed configuration, for example inside a catheter. The implant body 202 can define at least one groove such as a plurality of grooves 203 that extend into the inner or outer surfaces 202e-f along the folding edge 201. The grooves 203 can be define hinges that enhance the collapsibility of the implant body 202. The grooves 203 can be defined along one or more sections, up to the entirety of the folding edge 201, and can be defined in the inner surface 202e and/or the outer surface 202f in any combination as desired.

Referring now to FIGS. 5C-F, the implant body 202 can define one or more folding edges 201 and/or corresponding grooves 203, as desired. The implant body 202 depicted in FIG. 5C has a single folding edge 201 and a pair of corresponding grooves 203, thereby defining two plate segments 208 and thus two areas of contact between the inner surface 202e of the implant body 202 and the outer surface of the underlying bone 110. However, configuring the implant body 202 with a plurality of folding edges 201, thereby defining additional plate segments 208, can allow the implant body 202 to better conform to the outer surface of underlying structure, such as the underlying bone 110, for instance by providing more contact area between the inner surface 202e of the implant body 202 and the outer surface of the underlying bone 110. For example, the implant body 202 depicted in FIG. 5D has two folding edges 201 and corresponding grooves 203, thereby defining three equally dimensioned plate segments 208 and thus three areas of contact between the inner surface 202e of the implant body 202 and the outer surface of the underlying bone 110. In another example, the implant body 202 depicted in FIG. 5E has three folding edges 201 and corresponding grooves 203, thereby defining four equally dimensioned plate segments 208 and thus four areas of contact between the inner surface 202e of the implant body 202 and the outer surface of the underlying bone 110.

It should be appreciated that the folding edges 201 can be spaced equally or unequally apart from each other between the upper and lower edges 202c-d of the implant body 202, and thus that the plate segments 208 defined by the folding edges can be equally or differently dimensioned. For example, the implant body 202 depicted in FIG. 5F has seven folding edges 201 and corresponding grooves 203, thereby defining eight plate segments 208 and thus eight areas of contact between the inner surface 202e of the implant body 202 and the outer surface of the underlying bone 110. However, the outermost plate segments 208 located at the upper and lower edges 202c-d, respectively, have a greater lateral width than the six inner plate segments 208. It should further be appreciated that the implant body 202 can be configured with any number of folding edges 201 defined at any desired locations between the upper and lower edges 202c-d of the implant body 202, thereby defining plate segments 208 having any combination of lateral widths as desired. It should be appreciated that the number of folding edges 201, the location of the folding edges 201 with respect to the upper and lower edges 202c-d of the implant body 202, the lateral distance between the upper and lower edges 202c-d when the implant body 202 is in the expanded configuration, and/or the length of the implant body 202 can be defined based on the anatomy of the intended underlying bone 110 to which the implant will be attached, the amount of surface area on the underlying bone 110 to be fixedly enwrapped by the inner surface 202e of the implant 100, and the like.

Figure 6:
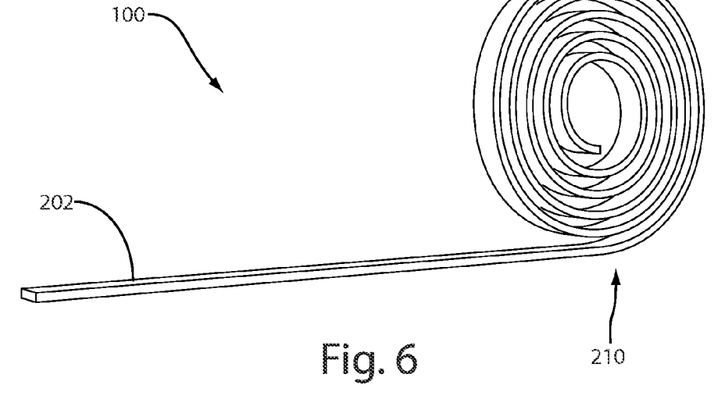
FIG. 6 is a perspective view of the expandable bone fixation implant illustrated in FIG. 5A in a rolled configuration.

The implant body 202 can be iterated from the expanded configuration to the collapsed configuration before implantation, or can initially be provided in the collapsed configuration. Alternatively, the implant body 202 can be provided in the collapsed configuration. The implant body 202 can be implanted into a patient using various techniques. In one example, the implant body 202 can be delivered into the patient's body using a sheath, such as that of a catheter, and iterated to the expanded configuration after the sheath is removed from the implant body 202. Alternatively, the implant body 202 can be iterated to its collapsed configuration and rolled upon itself in the longitudinal direction L, defining a rolled implant body 210 as illustrated in FIG. 6. The rolled implant body 210 can then be implanted and subsequently unrolled and iterated to the expanded configuration. It should be appreciated that the implant body 202 can also be provided as a rolled implant body 210. When provided as a rolled implant body 210, the implant body 202 can be cut from the rolled implant body 210 in a desired length and implanted into a patient using any suitable implantation method. It should further be appreciated the techniques described above for implantation of the implant body 202 and the rolled implant body 210 are merely examples, and that any method of implanting the implant body 202 and/or the rolled implant body 210 can be employed as desired.

Referring again to FIGS. 5A-F, once the implant body 202 has been implanted into a patient's body and/or maneuvered into position for attachment to an underlying bone, the implant body 202 can be iterated from the collapsed configuration illustrated in FIG. 2B to its expanded configuration with the use of a grasper tool, as described in more detail below. It should be appreciated that depending upon what material that is used to construct the implant body 202, that the implant body 202 may have shape memory characteristics such that the implant body 202 can expand at least partially, or completely unassisted, from the collapsed configuration to the expanded configuration, for instance when the implant body 202 is removed from a delivery sheath after being implanted. It should further be appreciated that the collapsed configurations of any of the plate bodies 202 depicted in FIGS. 5D-F can be configured differently from the collapsed configuration depicted in FIG. 5B, for example in accordance with the number of folding edges 201 and the lateral widths of the plate segments 208.

The implant body 202 can be configured with additional securement structures to enhance engagement between the inner surface 202e of the implant body 202 and the outer surface of the underlying bone to which the implant body 202 is attached. The securement structures can include the grip members described above with respect to the implant body 102, or any other securement structures as desired. Additionally, distinct areas of the inner surface 102e, up to the entirety of the inner surface 202e of the implant body 202, can be coated with bone growth enhancing materials, such as BMP, or the like.

Figure 7:
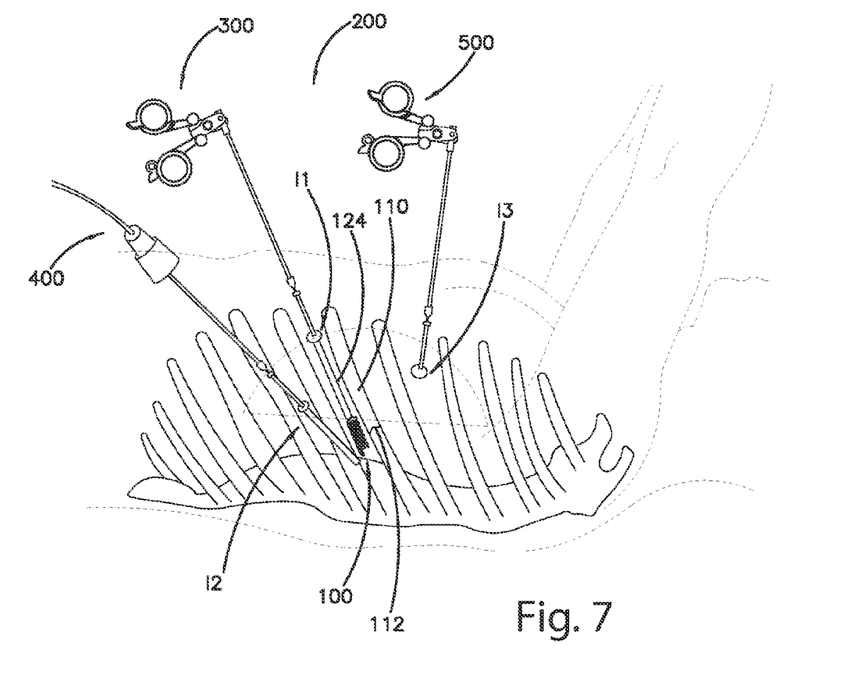
FIG. 7 is a side elevation view of an implant assembly for use in a percutaneous fixation procedure whereby the expandable bone fixation implant illustrated if
Figure 8:
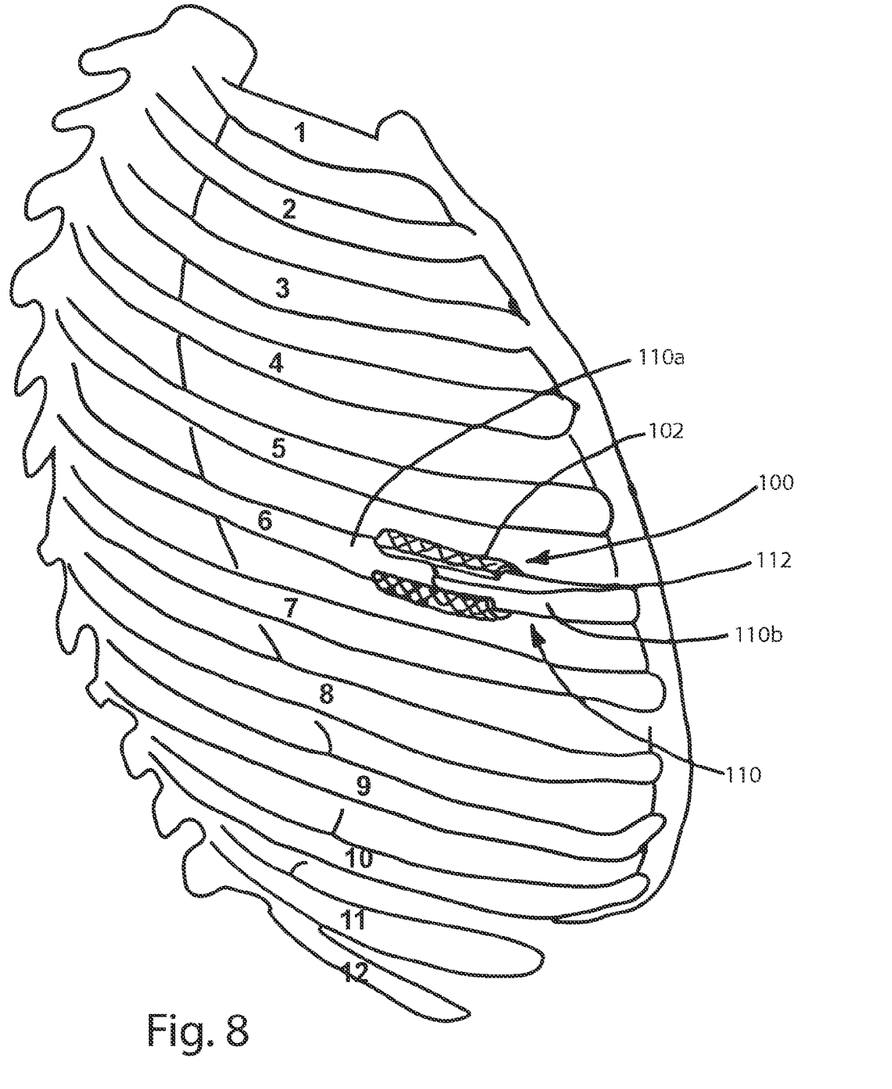
FIG. 8 is a perspective view of the expandable bone fixation implant attached to fractured rib using the implant assembly illustrated in FIG. 7.

Referring now to FIGS. 7-8, in operation, the expandable bone fixation implant 100 can be used for percutaneous or suitable alternative bone fixation procedures as desired. For example, a minimally invasive percutaneous bone fixation procedure can be performed in which a expandable bone fixation implant 100 is attached to an injured underlying bone 110, such as a rib that has sustained a fracture 112. An expandable bone fixation implant 100 appropriate for the particular procedure can be selected, such as a fixation implant 100 with the implant body 102. If the implant body 102 was not provided in its collapsed configuration, the implant body 102 can be iterated to its collapsed configuration in preparation for implantation.

A desired number of incisions, or ports, are made into appropriate locations of the patient's body. In the illustrated procedure, a first incision I1 is made to allow implantation of the expandable bone fixation implant 100 into the patient inside a catheter. A second incision 12 is made to allow the insertion of an instrument 400 configured with a camera, such as an endoscope. The endoscope can also be configured with a grasper component configured to operate the implant body 102 from the collapsed configuration to the expanded configuration and/or to maneuver the implant body 102 into position for attachment to the underlying bone 110. A third incision 13 can be made to allow the insertion of another instrument 500, such as a bone screw dispensing and/or driving tool or a second grasper tool. It should be appreciated that the number and locations of incisions illustrated and described herein are illustrative of a particular example fixation procedure, and that more or fewer incisions can be made at any location on a patient's body, depending for example upon the type of fixation procedure being performed.

The implant body 102, in its collapsed configuration, can be combined with a pair of tethered bone screws 116, an inflatable bladder 126, and a guide wire 128 in an implant assembly 200 and disposed within the sheath 124 of the catheter 300. It should be appreciated that the implant assembly 200 can be otherwise configured as described above. The catheter 300 may be selected based upon the volume displaced by the implant assembly 200, the type of implant body being implanted (e.g., 102, 202), whether the implant body is being implanted in the expanded or collapsed configuration, and so on, but will typically be selected from a range between a 4 mm (12 Fr) size to an 8 mm (24 Fr) size catheter. The catheter 300 can be inserted into the first incision or port and maneuvered into position in the vicinity of the underlying bone to which the implant body 102 is to be attached. As illustrated, the underlying bone 110 is the sixth rib, which has sustained a fracture 112. It is desirable to attach the implant body 102 to the underlying bone 110 such that both of the fractured bone segments 110a-b are encompassed by the implant body 102.

When the catheter 300 is positioned as desired, the sheath 124 can be retracted from the implant assembly 200, or the implant assembly 200 can otherwise be removed from the sheath 124, for example with the grasper tools of the instruments 400 and/or 500. The implant body 102 can then be iterated from the collapsed configuration to the expanded configuration. The implant body 102 can be iterated into its expanded configuration by inflating the bladder 126, may be operated into the expanded configuration through the use of the instruments 400 and/or 500, may expand to the expanded configuration at least partially due to shape memory characteristics of the material it is constructed from, or any combination thereof. Of course any additional securement structures, such as the above-described teeth, can be operated into their respective deployed configurations.

Once iterated to the expanded configuration, the implant body 102 can be further maneuvered into a final attachment position and secured to the underlying bone 110, for example via the grasper of one or more of the instruments 400 and/or 500, and placed into engagement with the underlying bone 110. The grasper of the instruments 400 and/or 500 can also be used to position the tethered bone screws 116 at desired locations so that they can be driven into the underlying bone 110 with the use of a driving instrument, thereby attaching, or securing, the implant body 102 to the underlying bone 110. Alternatively, if the implant body 102 of the implant assembly 200 is provided without tethered bone screws 116, the bone screws 116 can be dispensed, positioned, and/or driven into place by an instrument, such as a bone screw dispensing and/or driving tool. It should be appreciated that even if the implant body 102 is provided without tethered bone screws 116, that tethered bone screws 116 can still be employed in the fixation procedure. For example, the tethered bone screws 116 can be implanted via a separate instrument, and the distal ends 103b of the tethers 103 can be anchored to the implant body 102 and/or to surrounding structure, such as the underlying bone 110. It should further be appreciated that a single instrument or tool can be configured with the above-described grasper and bone screw dispensing and/or driving components.

The above-described fixation procedure can be similarly performed using a expandable bone fixation implant 100 configured with the implant body 202. It should be appreciated that the expandable bone fixation implant 100 is suitable for use in procedures other than a percutaneous fixation procedure. For example, the expandable bone fixation implant can be used as a supplementary fixation device with other types of bone plates, implants, and the like, or can be used in a prophylactic manner, for example to prevent further damage to hairline and/or stress fractures. It should further be appreciated that the expandable bone fixation implant 100 is suitable for use in stabilizing and providing fixation to underlying bones other than rib bones, for instance bones such as the ulna, the fibula, the clavicle, and the like.

It should be appreciated that components of the expandable bone fixation implant 100 and/or the implant assembly 200 can be provided in a variety of fixation kits. The components of the kits may be configured the same or differently. For example, within a single kit, plate bodies 102 and/or 202 can be provided that have varying lengths, mesh structures, curvatures, numbers of folding edges. Furthermore, the plate bodies 102 and/or 202 and can be provided with or without tethered bone screws having tethers of varying lengths, depending for example on the type of fixation procedure being performed. The kits may also be configured differently with respect to which components are included in the kits. For example, kits can be provided having any combination of the above-described components of the implant assembly 200 and/or any combination of the above-described instruments, or tools 300, 400, and 500.

Although the expandable bone fixation implant 100 and the implant assembly 200 have been described herein with reference to preferred embodiments or preferred methods, it should be understood that the words which have been used herein are words of description and illustration, rather than words of limitation. For example, it should be appreciated that the structures and/or features of components of the implant body 102 may be combined with or otherwise integrated with the structures and/or features of the implant body 202, unless otherwise indicated. Furthermore, it should be noted that although the expandable bone fixation implant 100 and the implant assembly 200 have been described herein with reference to particular structure, methods, and/or embodiments, the scope of the instant disclosure is not intended to be limited to those particulars, but rather is meant to extend to all structures, methods, and/or uses of the expandable bone fixation implant 100 and the implant assembly 200. Those skilled in the relevant art, having the benefit of the teachings of this specification, may effect numerous modifications to the expandable bone fixation implant 100 and the implant assembly 200 as described herein, and changes may be made without departing from the scope and spirit of the instant disclosure, for instance as recited in the appended claims.

What is claimed:

1. A bone fixation implant comprising:
an implant body that extends along a longitudinal axis between first and second opposed ends, the implant body including a plurality of interconnected resilient links that define a bone-facing surface and an opposed outer surface, the implant body further including a first edge and a second edge opposed to the first edge, the first and second edges extending 1) from the first end to the second end, and 2) from the bone-facing surface to the opposed outer surface,
wherein the resilient links are configured such that the implant body is operable between a collapsed configuration and an expanded configuration,
wherein the implant body includes a first segment and a second segment separated by a longitudinal fold edge, the first segment being folded over toward the second segment to define when the implant body is in the collapsed configuration, and
wherein the implant body is configured to be implanted into a body cavity in the collapsed configuration and fixed to the underlying bone in the body cavity in the expanded configuration.

2. The bone fixation implant as recited in claim 1, wherein the first and second opposed edges move relative to each other as the implant body is iterated between the collapsed and expanded configurations.

3. The bone fixation implant as recited in claim 2, wherein the first and second edges are aligned when the implant body is in the collapsed configuration.

4. The bone fixation implant as recited in claim 1, wherein the implant body is radially collapsible about the longitudinal axis.

5. The bone fixation implant as recited in claim 1, wherein the implant body further comprises a plurality of bone attachment locations.

6. The bone fixation implant as recited in claim 1, wherein the implant body is curved around the longitudinal axis between the first and second ends.

7. The bone fixation implant as recited in claim 1, wherein the implant body further comprises at least one tethered bone anchor.

8. The bone fixation implant as recited in claim 1, wherein the bone-facing surface has a plurality of securement structures formed thereon, the securement structures configured to engage the underlying bone.

9. The bone fixation implant as recited in claim 1, wherein the bone-facing surface is coated with a bone-growth enhancing material.

10. The bone fixation implant as recited in claim 1, wherein the first and second cross-sectional dimensions extend along a straight line that passes through the longitudinal axis.

11. The bone fixation implant as recited in claim 10, wherein the longitudinal axis is a central longitudinal axis.

12. The bone fixation implant as recited in claim 1, wherein the plurality of interconnected resilient links define a plurality of openings, each of plurality of openings have a first dimension when the implant body is in the collapsed configuration and a second dimension that is greater than the first dimension when the implant body is in the expanded configuration.

13. The bone fixation implant as recited in claim 1, wherein implant body is made of shape memory alloy.

14. A bone fixation kit comprising:
a first bone fixation implant that extends along a longitudinal axis so as to define a first length defined between a first end of the first bone fixation implant and a second end of the first bone fixation implant along the longitudinal axis, the first bone fixation implant including a first plurality of interconnected resilient links, the first bone implant including a first edge and a second edge opposed to the first edge, the first and second edges extends from the first end to the second end of the first bone fixation implant;
a second bone fixation implant that extends along a second longitudinal axis so as to define a second length defined between a first end of the second bone fixation implant and a second end of the second bone fixation implant along the second longitudinal axis, the second bone fixation implant including second plurality of interconnected resilient links, the second bone implant including a first edge and a second edge opposed to the first edge, the first and second edges of the second bone implant extend from the first end to the second end of the second bone fixation implant; and
a plurality of bone anchors configured to attach the first and second bone fixation implants to one or more respective underlying bones,
wherein the first and second pluralities of resilient links are configured such that the first and second bone fixation implants are expandable from a collapsed configuration to an expanded configuration,
wherein at least one of the first and second bone fixation implants includes a first segment and a second segment separated by a longitudinal fold edge, the first segment being folded over toward the second segment to define when the implant body is in the collapsed configuration, and
wherein the first and second bone fixation implants are configured for implantation into a patient in the collapsed configuration and expandable for attachment to the respective one or more underlying bones.

15. The bone fixation kit as recited in claim 14, wherein the first and second lengths are different.

16. The bone fixation kit as recited in claim 14, wherein at least one of the plurality of bone anchors are tethered to at least one of the first and second bone fixation implants.

17. The bone fixation kit as recited in claim 14, wherein at least one of the first and second bone fixation implants is radially collapsible about a respective longitudinal axis.

18. The bone fixation kit as recited in claim 14, wherein at least one of the first and second bone fixation implants is transversely collapsible upon itself around a respective longitudinal folding edge.

19. A method of fixing a fractured rib that defines a first bone segment and a second bone segment separated from the first bone segment by a fracture, the method comprising:
implanting, in a collapsed configuration, the bone fixation implant into a body cavity of a patient that contains the fractured rib, wherein the bone fixation implant defines a first outer cross-sectional dimension when in the collapsed configuration;

after the implanting step, iterating the bone fixation implant to an expanded configuration, such that the bone fixation implant defines a second outer cross-sectional dimension that is greater than the first outer cross-sectional dimension; and bringing a bone-facing surface of the of the bone fixation implant against an outer surface of the first and second bone segments across the fracture.

20. The method of bone fixation as recited in claim 19, wherein the method further comprises securing the bone fixation implant to the underlying bone with at least one bone anchor.

21. The method of bone fixation as recited in claim 19, wherein the at least one bone anchor is tethered to the bone fixation implant.

\* \* \* \* \*